United States Patent [19]

Kurono et al.

[11] Patent Number: 4,656,303

[45] Date of Patent: Apr. 7, 1987

[54] NOVEL RESOLUTION METHOD OF RACEMIC MIXTURE

[75] Inventors: Masayasu Kurono, Nagoya; Takafumi Iida, Kasugai; Katsuhiro Hayashi, Kakamigahara; Kunio Yagi, Nagoya, all of Japan

[73] Assignee: Institute of Applied Biochemistry, Gifu, Japan

[21] Appl. No.: 663,923

[22] Filed: Oct. 23, 1984

[30] Foreign Application Priority Data

Jan. 20, 1984 [JP] Japan ................................... 59-7259

[51] Int. Cl.$^4$ .......................................... C07C 121/43
[52] U.S. Cl. .................................... 558/354; 558/451; 560/106; 260/503; 562/443; 562/582; 562/585
[58] Field of Search ........................ 260/465.5 R, 503; 562/443, 582, 585; 560/106; 558/354, 451

[56] References Cited

U.S. PATENT DOCUMENTS 3,167,566  1/1965  Overby ............................... 548/498

FOREIGN PATENT DOCUMENTS 40-3891  3/1965  Japan .

OTHER PUBLICATIONS

Strack, et al., "Hoppe Seyler's Zeitschrift fur Physiologische Chemie", Band 318, (1960), Summary, p. 137.
Organic Syntheses, vol. 5, 1973, John Wiley and Sons, pp. 932–936.
Journal of the Pharmaceutical Society of Japan, vol. 81, No. 5 (1961), pp. 778, 779 and 780.

Primary Examiner—Joseph Paul Brust
Attorney, Agent, or Firm—Armstrong, Nikaido, Marmelstein & Kubovcik

[57] ABSTRACT

A novel resolution method of a racemic mixture, wherein four kinds of salts are dissolved in a resolving solvent to fractionally crystallize a desired optically active isomer through an exchange reaction between counter ions.

10 Claims, No Drawings

NOVEL RESOLUTION METHOD OF RACEMIC MIXTURE

BACKGROUND OF THE INVENTION

1. Field of the Invention

The present invention relates to a novel resolution method of a racemic mixture to obtain a desired optically active isomer thereof.

2. Prior Art

As a conventional resolution method of a racemic mixture into optically active isomers thereof, there is a so-called Diastereomer Method, wherein two diastereomer salts are resolved on the basis of their solubility differences after treating a racemic mixture with an optically active compound as a resolving agent. When such a Diastereomer Method is carried out in a commercial scale, various improvements have been tried, but none of them could overcome an inherent drawback in the method, namely a low resolution efficiency.

SUMMARY OF THE INVENTION

An object of the present invention is to provide a novel resolution method of a racemic mixture, which basically utilizes a resolution principle in the conventional Diastereomer Method but has high resolution efficiency and economical merit.

According to the invention, the object can be accomplished by a novel resolution method of a racemic mixture into optically active isomers thereof, which comprises steps of mixing (A) two diastereomer salts formed by treating a racemic starting material with an optically active compound as a resolving agent and (B) two salts selected from diastereomer salts and racemic salts, formed by treating the racemic starting material with a compound which is either optically pure or optically inactive, and which is different from said resolving agent, dissolving the resulting mixture in a resolving solvent and fractionally crystallizing a desired diastereomer salt which is enriched through an exchange reaction between counter ions.

The invention is based upon a finding that an exchange reaction of counter ions among salts occurs during a fractional crystallization step thereof to increase a yield of desired crystals, provided that the fractional crystallization is carried out in a solution containing four kinds of salts and the desired salt is the most crystallizable one among them to be precipitated depending on solubility differences thereof.

In order to clarify the principle of this invention, reference is made to Table 1, in which the present method of optical resolution is compared with a conventional Diastereomer Method. For purposes of this Table, the following conventions are assumed:

1. The racemic starting material is a base consisting of D and L-isomers (referred to as D and L),
2. The optically active compound employed as a resolving agent is an acid (referred to as X),
3. Each diastereomer salt consists of D or L and X (referred to as $D^{\oplus}X^{\ominus}$ and $L^{\oplus}X^{\ominus}$),
4. Each of secondary salts consists of D or L and an acid which is different from X (referred to as $D^{\oplus}Y^{\ominus}$ and $L^{\oplus}Y^{\ominus}$), wherein the acid Y may be of optically active or inactive but may not be racemic,
5. The order of solubility for a resolving solvent is $L^{\oplus}X^{\ominus} < D^{\oplus}X^{\ominus} < L^{\oplus}Y^{\ominus} \simeq D^{\oplus}Y^{\ominus}$ and in other words, $L^{\oplus}X^{\ominus}$ is the most crystallizable salt among them,
6. Symbols show followings:
   $D^{\ominus}$: cation of D,
   $L^{\ominus}$: cation of L,
   $X^{\oplus}$: anion of X,
   $Y^{\oplus}$: anion of Y,
7. Each of other symbols n and m shows a ratio of equivalent of each salt.

TABLE 1

| | salts employed for crystallization | theoretical amount of salts (after crystallization) | |
|---|---|---|---|
| | | mother liquid | crystals |
| conventional method | $nD^{\oplus}X^{\ominus} + nL^{\oplus}X^{\ominus}$ | $nD^{\oplus}X^{\ominus}$ | $nL^{\oplus}X^{\ominus}$ |
| invention method | $nD^{\oplus}X^{\ominus} + nL^{\oplus}X^{\ominus} +$ $mD^{\oplus}Y^{\ominus} + mL^{\oplus}Y^{\ominus}$ | (1) n = m $(n + m)D^{\oplus}Y^{\ominus} = 2nD^{\oplus}Y^{\ominus}$ | $(n + m)L^{\oplus}X^{\ominus} = 2nL^{\oplus}X^{\ominus}$ |
| | | (2) n < m $(m - n)L^{\oplus}Y^{\ominus} + (m + n)D^{\oplus}Y^{\ominus}$ | $2nL^{\oplus}X^{\ominus}$ |
| | | (3) n > m $2mD^{\oplus}Y^{\ominus}$ | $(n - m)D^{\oplus}X^{\ominus} + (n + m)L^{\oplus}X^{\ominus}$ |

As shown in the Table, when the mixture of these four salts is subjected to a fractional crystallization with use of a resolving solvent in accordance with the present invention, the most crystallizable salt ($L^{\oplus}X^{\ominus}$) is first crystallized out in a mother liquid depending on its solubility difference and then, an exchange reaction of counter ions occurs between $D^{\oplus}X^{\ominus}$ and $L^{\oplus}Y^{\ominus}$ to crystallize out an additional amount of $L^{\oplus}X^{\ominus}$, so that a total amount of the desired $L^{\oplus}X^{\ominus}$ becomes larger than an amount thereof which was contained as one of structural components in the racemic starting material.

The invention can also be applied, even if the racemic starting material is not a basic but acidic compounds. In this case, basic materials should be selected for the resolving agent and the like. For carrying out the invention, it is preferable to select a ratio of n to m as a value smaller than 1.

In the conventional Diastereomer Method, an expensive resolving agent is generally required in a large amount. While in the method according to the present invention, a part of such expensive resolving agent (optically active compounds) is replaced with an agent which is easily available at a reasonable price and in spite of that, a high efficiency of resolution can be attained. So, this method is quite preferable for resolution of a racemic mixture as an industrial procedure.

The method according to the invention can be applied to a resolution of various racemic mixtures. A few typical examples shall be shown as follows.

1. preparation of 1-(R) or 1-(S)-7,7-dimethyl-2-oxobicyclo[2,2,1]heptane-1-methanesulfonic acid (hereinafter referred to as L(−) or D(+)-10-camphorsulfonic acid) by resolution of 1-(RS)-7,7-dimethyl-2-oxobicyclo[2,2,1]heptane-1-methanesulfonic acid (hereinafter referred to as DL-10-camphorsulfonic acid)

2. preparation of (R) or (S)-1-phenylethylamine (hereinafter referred to as D(+) or L(−)-1-phenylethylamine) by resolution of (RS)-1-phenylethylamine (hereinafter referred to as DL-1-phenylethylamine)

3. preparation of 2-(R) or 2-(S)-3-cyano-2-hydroxypropyltrimethylammonium salt (hereinafter referred to as L(−) or D(+)-carnitinenitrile salt) by resolution of 2-(RS)-3-cyano-2-hydroxypropyltrimethylammonium salt (hereinafter referred to as DL-carnitinenitrile salt)

Each of such resolutions may be carried out with following steps.

First Step

The racemic starting material and the optically active resolving agent are mixed in a suitable solvent and then a resulting solution is concentrated and dried in vacuo to yield a mixture of two salts.

Second Step

The racemic starting material and the optical inactive compound is treated in a manner similar to that in the first step to give another mixture of two salts.

Third Step

The salt mixtures obtained through the first and second steps are mixed in an suitable ratio and then dissolved in a resolving solvent. The resulting solution is subjected to fractional crystallization to obtain a desired optically active isomer.

In the preparation of D(+) or L(−)-10-camphorsulfonic acid, examples of the optically active basic compound to be used are D(−) or L(+)-α-phenylglycine, cinchonine, cinchonidine, quinine, brucine, (+) or (−)-ephedrine and the like. Examples of the optically inactive basic compound to be used are hydroxides such as sodium hydroxide, potassium hydroxide and the like and amines such as ammonia, methylamine, dimethylamine, trimethylamine and the like.

In the preparation of D(+) or L(−)-1-phenylethylamine, examples of the optically active acidic compound to be used are L(+) or D(−)-tartaric acid, D(+) or L(−)-malic acid, D(+) or L(−)-10-camphorsulfonic acid, D(+) or L(−)-camphoric acid and the like, examples of the optically inactive acidic compound to be used are inorganic acids such as hydrogen chloride, hydrogen bromide, nitric acid, sulfuric acid, perchloric acid and the like and organic acids such as acetic acid, butyric acid, formic acid, benzoic acid, oxalic acid, methanesulfonic acid and the like.

In the preparation of D(+) or L(−)-carnitinenitrile salt, examples of the optically active acidic compound to be used are L(−) or D(+)-10-camphorsulfonic acid, D(−) or L(+)-tartaric acid, D or L-dibenzoyltartaric acid and the like, examples of the optically inactive acid to be used are inorganic acids such as hydrogen chloride, hydrogen bromide, nitric acid, sulfuric acid, perchloric acid and the like, and organic acids such as acetic acid, butyric acid, benzoic acid, oxalic acid and the like.

In either case, examples of the resolving solvent to be used are protic solvents such as water, methanol, ethanol and the like. Particularly, blended solvent such as aqueous ethanol are preferred since it can be readily available.

PREFERRED EMBODIMENTS OF INVENTION

Please note that following abbreviations are employed in following examples.

| | |
|---|---|
| DL-α-phenylglycine | DL-PG |
| D(−)-α-phenylglycine | D(−)-PG |
| DL-10-camphorsulfonic acid | DL-CSA |
| D(+)-10-camphorsulfonic acid | D(+)-CSA |
| L(−)-10-camphorsulfonic acid | L(−)-CSA |
| D(−)-α-phenylglycine DL-10-camphorsulfonate | D(−)-PG.DL-CSA |
| D(−)-α-phenylglycine D(+)-10-camphorsulfonate | D(−)-PG.D(+)-CSA |
| ammonium DL-10-camphorsulfonate | AM.DL-CSA |
| dimethylammonium DL-10-camphorsulfonate | DMAM.DL-CSA |
| DL-1-phenylethylamine | DL-PEA |
| L(−)-1-phenylethylamine | L(−)-PEA |
| L(+)-tartaric acid | L(+)-T |
| DL-1-phenylethylammonium L(+)-tartrate | DL-PEA.L(+)-T |
| L(−)-1-phenylethylammonium L(+)-tartrate | L(−)-PEA.L(+)-T |
| DL-1-phenylethylammonium hydrochloride | DL-PEA.Cl |
| DL-caritinenitrile | DL-CARCN |
| DL-carnitinenitrilechloride | DL-CARCN.Cl |
| DL-carnitinenitrile D(+)-10-camphorsulfonate | DL-CARCN.D(+)-CSA |
| D(+)-γ-trimethylamino-β-hydroxybutyronitrile camphorsulfonate | D(+)-10-DL-CARCN.D(+)-CSA |
| Di-(DL-carnitinenitrile) (+)-tartrate | D(DL-CARCN).L(+)-T |

EXAMPLE 1

Fractional Crystallization Employing Equivalent Amounts of D(−)-PG.DL-CSA and AM.DL-CSA (1) Preparation of D(−)-PG.DL-CSA DL-CSA (10.00 g, 0.0430 mole) was dissolved in hot distilled water (82 ml). To this solution D(−)-PG (6.51 g, 0.0430 mole) was added and dissolved. The resulting solution was concentrated with a rotary evaporator and dried to give D(−)-PG.DL-CSA [16.47 g, 99.8% yield, $[\alpha]_D^{20} -62.5°$ (C=4.0, 1N-HCl), $[\alpha]_{436}^{20} -128.7°$ (C=4.3, 1N-HCl)].

(2) Preparation of AM.DL-CSA

DL-CSA (10.0 g, 0.043 mole) was dissolved in hot distilled water (30 ml). The solution was neutralized with 28% aqueous ammonia (5 ml) and the resulting solution was concentrated and dried in vacuo to give AM.DL-CSA (10.69 g, 99.6% yield).

(3) Fractional crystallization

A mixture of D(−)-PG.DL-CSA (3.00 g, 7.82 mmole) and AM.DL-CSA (1.95 g, 7.82 mmole) was dissolved in hot distilled water (4.5 ml). This solution was seeded with crystals of D(−)-PG.D(+)-CSA ($[\alpha]_D^{20}+50.0°$ (C=5.2, 1N-HCl), $[\alpha]_{436}^{20}-90.7°$ (C=5.2, 1N-HCl)) at 65° C. and allowed to cool. The precipitated crystals were collected by filtration and dried in vacuo to give crystals (2.12 g, $[\alpha]_{436}^{20}-93.4°$ (C=2.2, 1N-HCl)). The crystals contained 99% D(−)-PG.(+)-CSA salts by weight. The yield of D(−)-PG salts was 70.0% on the basis of the starting D(−)-PG.DL-CSA.

EXAMPLE 2

Fractional Crystallization Employing AM.DL-CSA At The Molar Ratio To D(−)-PG.DL-CSA of 1.25

A mixture of D(−)-PG.DL-CSA (3.00 g, 7.82 mmoles) and AM.DL-CSA (2.44 g, 9.78 mmoles) was dissolved in hot distilled water (3.8 ml). This solution was seeded with crystals of D(−)-PG.D(+)-CSA at 70° C. and allowed to cool. The precipitated crystals were collected by filtration and dried in vacuo to give crystals [2.43 g, $[\alpha]_{436}^{20}-90.2°$ (C=2.4, 1N-HCl)]. The crystals contained 95% D(−)-PG.D(+)-CSA salts by weight. The yield of D(−)-PG salts was 81.0% on the basis of the starting D(−)-PG.DL-CSA.

EXAMPLE 3

Fractional Crystallization Employing DMAM.DL-CSA at the Molar Ratio to D(−)-PG.DL-CSA of 1.25

(1) Preparation of DMAM.DL-CSA

DL-CSA (10.00 g, 0.0430 mole) was dissolved in hot distilled water (30 ml). This solution was neutralized with 50% aqueous dimethylamine (5 g), and the resulting solution was concentrated and dried in vacuo to give DMAM.DL-CSA (11.84 g, 99.1% yield).

(2) Fractional crystallization

A mixture of D(−)-PG.DL-CSA (3.00 g, 7.82 mmoles) and DMAM.DL-CSA (2.71 g, 9.78 mmoles) was dissolved in hot distilled water (3.3 ml). This solution was seeded with crystals of D(−)-PG.D(+)-CSA at 70° C. and allowed to cool. The precipitated crystals were collected by filtration and dried in vacuo to give crystals [2.56 g, $[\alpha]_{436}^{20}-92.0°$ C. (C=2.6, 1N-HCl)]. The crystals contained 93% D(−)-PG.D(+)-CSA salts by weight. The yield of D(−)-PG salts was 80.0% on the basis of the starting D(−)-PG.DL-CSA.

EXAMPLE 4

Fractional Crystallization Employing Equivalent Amounts of D(−)-PG.DL-CSA and DMAM.DL-CSA (1) The first fractional crystallization A mixture of D(−)-PG.DL-CSA (20.0 g, 52.1 mmoles) and DMAM.DL-CSA (14.46 g, 52.1 mmoles) was dissolved in hot distilled water (27.6 ml). This solution was seeded with crystals of D(−)-PG.D(+)-CSA at 70° C. and allowed to cool. The precipitated crystals were collected by filtration and dried in vacuo to give crystals [15.86 g, $[\alpha]_{436}^{20}-94.1°$ (C=3.1, 1N-HCl)]. The crystals contained 97% D(−)-PG.D(+)-CSA salts by weight. A yield of D(−)-PG salts was 76.9% on the basis of the starting D(−)-PG.DL-CSA.

(2) The second fractional crystallization

The crystals (13.00 g) prepared in the above (1) were dissolved in hot distilled water (30 ml). The resulting solution was seeded with crystals of D(−)-PG.D(+)-CSA at 70° C. and allowed to cool. The precipitated crystals were collected by filtration and dried in vacuo to give crystals (10.53 g, 81.0% yield). The crystals contained more than 99% D(−)-PG salts by weight. The yield of D(−)-PG.D(+)-CSA salts was 62.2% on the basis of the starting D(−)-PG.DL-CSA. Physical properties of the crystals are shown in the following Table.

| m.p. | 201–203° C. |
|---|---|
| Specific Rotation | $[\alpha]_D^{20}$-50.0° (C = 3.6, 1N—HCl)<br>$[\alpha]_{436}^{20}$-90.5° (C = 3.6, 1N—HCl) |
| $IR\nu_{cm^{-1}}^{KBr}$: | 3300–3000 (—$\overset{+}{N}H_3$, —COOH), 1750 (Camphor —C=O), 1705 (phenylglycine-C=O), 1150–1200 (—$SO_3^{\ominus}$) |
| $NMR\delta_{90Mc}^{DMSO-d6}$: | 0.74 (3H, s), 1.04 (3H, 2), 1.20–2.85 (7H, m), 2.40 (2H, dd), 2.92 (2H, dd), 5.09 (1H, s), 7.4 (5H, m) |

REFERENCE EXAMPLE 1

Preparation of D(+)-CSA From D(−)-PG.D(+)-CSA

The crystals (8.00 g, 20.9 mmole) prepared in Example 4 were dissolved in hot distilled water (30 ml). The resulting solution was neutralized to pH=7.0 with 5N-aqueous sodium hydroxide solution and allowed to cool at 0° C. The precipitated crystals were collected by filtration and dried in vacuo to give 2.90 g of D(−)-PG (91.8% yield). The filtrate was passed through a column of a strong acidic cation exchange resin (100 mmoles equivalent; H form) and the effluent solution was concentrated and dried in vacuo by a rotary evaporator to give D(+)-CSA (4.86 g, 100% yield). Physical properties of the crystals are shown in the following Table.

| Specific Rotation: | $[\alpha]_D^{20}$ + 21.0° (C = 5.2, H$_2$O), m.p. 195–197° C. |
|---|---|
| $IR\nu_{cm^{-1}}^{KBr}$: | 1730 (C=O), 1110–1200 ($SO_3^-$) |
| $NMR\delta_{90Mc}^{DMSO-d6}$: | 0.78 (3H, s), 1.05 (3H, s), 1.20–2.70 (7H, m), 2.60 (2H, dd), 3.07 (2H, dd) |

EXAMPLE 5

Fractional Crystallization Employing Equivalent Amounts of DL-PEA.L(+)-T and DL-PEA.Cl (1) Preparation of DL-PEA.L(+)-T L(+)-T (24.76 g, 0.165 mole) was dissolved in methanol (90 ml) and to this solution a solution of DL-PEA (20.00 g, 0.165 mole) diluted with methanol (13 ml) was added. The resulting solution was concentrated and dried in vacuo with a rotary evaporator to give crude crystals (45.69 g, 102% yield) of DL-PEA.L(+)-T ($[\alpha]_{405}^{20}+27.2°$ (C=4.6, H$_2$O), $[\alpha]_D^{20}+15.30$ (C=4.4, H$_2$O), m.p. 167°–170° C.).

(2) Preparation of DL-PEA.Cl

To a solution of 12N-aqueous hydrochloric acid (8.2 ml) was added DL-PEA (10.0 g, 0.0825 moles) dissolved in distilled water (15 ml) with cooling. The resulting solution was concentrated and dried in vacuo to give crude crystals (13.0 g, 100.7% yield) of DL-PEA.Cl.

(3) Fractional crystallization

A mixture of DL-PEA.L(+)-T (30.00 g, 0.111 mole) and DL-PEA.Cl (17.43 g, 0.111 mole) was dissolved in hot methanol (280 ml) and then concentrated with a rotary evaporator to a volume of 172 ml. The resulting solution was seeded with crystals of L(−)-PEA.L(+)-T ($[\alpha]_D^{20}+13.1°$ C. (C=5.0, H$_2$O), $[\alpha]_{405}^{20}+22.4°$ (C=4.9, H$_2$O), m.p. 179°–181° C.) at 67° C. and allowed to cool. The precipitated crystals were collected by filtration, washed with a small amount of ethanol, and dried in vacuo to give crystals (20.32 g) (primary crystals). The crystals contained 99.6% L(+)-T salts by weight. The yield of L(−)-PEA.L(+)-T salts was 67.5% on the basis of the starting DL-PEA.L(+)T. The filtrate was concentrated to a volume of 33 ml with a rotary evaporator, seeded with crystals of L(−)-PEA.L(+)T, and allowed to cool. The precipitated crystals were collected by filtration, washed with a small amount of ethanol, and dried in vacuo to give crystals (3.30 g) (secondary crystals). The crystals contained 99.1% L(+)-T salts by weight. The yield of L(−)-PEA.L(+)-T salts was 10.9% on the basis of the starting DL-PEA.L(+)-T. The total yield of L(+)-T salts in the primary and secondary crystals was 78.4% on the basis of the starting DL-PEA.L(+)-T. Physical properties of these crystals are shown in the following Table.

|  | Specific Rotation |
|---|---|
| Primary Crystals | $[\alpha]_{405}^{20}$ + 22.65° (C = 5.9, H$_2$O), m.p. 178–181.5° C. |
|  | $[\alpha]_D^{20}$ + 13.17° (C = 5.0, H$_2$O) |
| Secondary Crystals | $[\alpha]_{405}^{20}$ + 23.12° (C = 6.8, H$_2$O) |
| Primary Crystals |  |
| IR$\nu_{cm^{-1}}^{KBr}$: | 3500–3150 (—$\overset{+}{N}$H$_3$), 3000 broad (—COOH), 1730 (—C=O), 1600, 1410 (—COO$\ominus$) |
| NMR$\delta_{90Mc}^{D_2O}$: | 1.67 (3H, d, J = 7.1 Hz), 4.49 (2H, s), 4.52 (1H, m), 7.5 (5H, m) |

EXAMPLE 6

Fractional Crystallization Employing Equivalent Amounts of DL-PEA.L(+)-T and DL-PEA.Cl A mixture of DL-PEA.L(+)-T (10.00 g, 36.9 mmoles) and DL.PEA.Cl (5.81 g, 36.9 mmoles) was obtained by steps 1 and 2 of Example 5 dissolved in hot methanol (95 ml). The resulting solution was concentrated to a volume of 58 ml, seeded with crystals of L(−)-PEA.L(+)-T, and allowed to cool. The precipitated crystals were collected by filtration, washed with a small amount of ethanol, and dried in vacuo to give crystals (6.98 g, $[\alpha]_D^{20}+13.1°$ (C=5.3, H$_2$O), $[\alpha]_{405}^{20}+22.5°$ (C=5.3, H$_2$O), m.p. 178°–181.5° C.) (primary crystals). The crystals contained 99.3% L(−)-PEA.L(+)-T salts by weight. The yield of L(+)-T salts was 69.3% on the basis of the starting DL-PEA L(+)-T. The resulting solution was concentrated to a volume of 11.7 ml. The resulting solution was seeded with crystals of L(−)-PEA.L(+)-T and allowed to cool. The precipitated crystals were collected by filtration, washed with a small amount of ethanol, and dried in vacuo to give crystals (1.32 g, $[\alpha]_D^{20}+13.1°$ (C=3.4, H$_2$O)) (secondary crystals). The crystals contained 97.1% L(+)-T salts by weight. The yield of L(−)-PEA.L(+)-T salts in the primary and secondary crystals was 82.1% on the basis of the starting DL-PEA.L(+)-T. The total yield of L(−)-PEA.L(+)-T in the primary and secondary crystals was 79.4% on the basis of the starting DL-PEA.L(+)-T.

EXAMPLE 7

Fractional Crystallization Employing DL-PEA.Cl at the Molar Ratio to DL-PEA.L(+)-T of 1.2

A mixture of DL-PEA.L(+)-T (7.00 g, 25.8 mmoles) and DL-PEA.Cl (4.88 g, 31.0 mmoles) was dissolved in hot methanol (72 ml). The resulting solution was concentrated to a volume of 36 ml, seeded with crystals of L(−)-PEA.L(+)-T, and allowed to cool. The precipitated crystals were collected by filtration, washed with a small amount of ethanol, and dried in vacuo to give crystals (4.38 g, $[\alpha]_D^{20}+13.0°$ (C=5.4, H$_2$O), $[\alpha]_{405}^{20}+22.7°$ (C=5.5, H$_2$O)) (primary crystals). The crystals contained 99.2% L(+)-T salts by weight. The yield of L(−)-PEA.L(+)-T salts was 62.1% on the basis of the starting DL-PEA.L(+)-T. The filtrate was concentrated to a volume of 7.7 ml, seeded with crystals of L(−)-PEA.L(+)-T, and allowed to cool. The precipitated crystals were collected by filtration, washed with a small amount of ethanol, and dried in vacuo to give crystals (1.42 g, $[\alpha]_D^{20}+13.9°$ (C=4.8, H$_2$O)) (secondary crystals). The crystals contained 85.8% L(+)-T salts by weight. The yield of L(+)-T salts was 17.4% on the basis of the starting DL-PEA.L(+)-T. The total yield of L(−)-PEA.L(+)-T salts in the primary and secondary crystals was 79.5% on the basis of the starting DL-PEA.L(+)-T.

REFERENCE EXAMPLE 2

Preparation of L(−)-PEA From L(−)-PEA.L(+)-T

The primary crystals (18.00 g, 66.4 mmoles) in Example 5 was dissolved in deionized water (100 ml) and treated with 20 ml of 10N-aqueous sodium hydroxide. The resulting mixture was shaken with ether in 4 times (80 ml×4). After the combined ether extracts had been washed with saturated aqueous sodium chloride (50 ml) and dried over anhydrous sodium sulfate, the sodium sulfate was removed from the solution by filtration. The filtrate was concentrated with a rotary evaporator to give a residual colorless liquid (7.86 g, 97.8% crude yield). The liquid was distilled under reduced pressure to give the first distillate (1.43 g, b.p. 68°–69° C./13 mmHg) and subsequently the second distillate (5.88 g, 73.1% yield, b.p. 69° C./13 mmHg). The physical properties of the second distillate are shown in the following Table.

| Specific rotation | $[\alpha]_D^{20}$-38.9° (neat) (d = 0.95) |
|---|---|
| IR$\nu_{cm^{-1}}^{(neat)}$: | 3368, 3300 ($\nu$-NH$_2$), 1600 broad ($\delta$-NH$_2$), 2955, 2860 ($\nu_{as}$-CH$_3$), 1450 ($\delta_{as}$-CH$_3$) |
| NMR$\delta_{90Mc}^{DMSO-d6}$: | 1.24 (3H, d, J = 6.6 Hz), 3.98 (1H, q, J = 6.6 Hz), 7.3 (5H, m) |

EXAMPLE 8

Fractional Crystallization by Employing Equivalent Amounts of DL-CARCN.Cl and DL-CARCN.D(+)-CSA (1) Preparation of DL-CARCN.D(+)-CSA DL-CARCN.Cl (89.3 g, 0.50 mole) in distilled water (20 ml) was passed through a column of a strong anion exchange resin (1.50 moles equivalent; OH form) and the effluent solution was neutralized to pH=7.0 with D(+)-CSA. The resulting solution was concentrated to dryness to give crude crystals (182.5 g, 97.5% yield) of DL-CARCN.CSA ($[\alpha]_D^{20}$+14.4° (C=5.0, H$_2$O)).

(2) The first crystallization

A mixture of DL-CARCN.D(+)CSA (37.45 g, 0.10 moles) and DL-CARCN.Cl (17.87 g, 0.10 mole) was dissolved in hot deionized water (17.5 ml). The resulting solution was seeded with crystals of D(+)-CARCN.D(+)-CSA at 70° C. and allowed to cool. The precipitated crystals were collected by filtration, washed with methanol (3 ml), and dried in vacuo to give crystals (28.30 g, $[\alpha]_D^{20}$+23.0° (C=5.0, H$_2$O)). The crystals contained 93.2% D(+)-CSA salts by weight. The yield of D(+)-CARCN.D(+)-CSA salts was 72.4% on the basis of the starting DL-CARCN.-D(+)-CSA.

(3) The second crystallization

The crystals (10.00 g) prepared in the above (2) were dissolved in hot 80% aqueous ethanol (11 ml). The resulting solution was seeded with crystals of D(+)-CARCN.D(+)-CSA at 60° C. and allowed to cool. The precipitated crystals were collected by filtration, washed with ethanol (1 ml), and dried in vacuo to give crystals (8.24 g $[\alpha]_D^{20}$+25.8° (C=5.0, H$_2$O), m.p. 198.5°–199° C.). The crystals contained 99.2% D(+)-CARCN.D(+)-CSA salts by weight. The yield of D(+)-CSA salts was 63.4% on the basis of the starting DL-CARCN.D(+)-CSA.

EXAMPLE 9

Fractional Crystallization Employing DL-CARCN.Cl at the Molar Ratio to DL-CARCN.D(+)-CSA of 1.25

(1) The first crystallization

A mixture of DL-CARCN.D(+)-CSA (200.0 g, 0.534 mole) and DL-CARCN.Cl (119.3 g, 0.668 mole) was dissolved in hot deionized water (92.5 ml). The resulting solution was seeded with crystals of D(+)-CARCN.D(+)-CSA at 80° C. and allowed to cool. The precipitated crystals were collected by filtration, washed with 90% aqueous ethanol (18 ml), and dried in vacuo to give crystals (177.0 g) (primary crystals). The crystals contained 95.4% D(+)-CARCN.D(+)-CSA salts by weight. The yield of D(+)-CSA salts was 84.4% on the basis of the starting DL-CARCN.D(+)-CSA.

(2) The second crystallization

The crystals (130.0 g) prepared in the above (1) were dissolved in hot deionized water (44.2 ml). The resulting solution was seeded with crystals of D(+)CARCN.D(+)-CSA at 82° C. and allowed to cool. The precipitated crystals were collected by filtration, washed with 90% aqueous ethanol (10 ml) and dried in vacuo to give crystals (93.1 g) (secondary crystals). The crystals contained 99.7% D(+)-CARCN.-D(+)-CSA salts by weight. The yield of D(+)-CSA salts was 63.1% on the basis of the starting DL-CARCN.D(+)-CSA. Subsequently, the mother liquor was allowed to stand at 4° C. for 4 days to precipitate crystals (9.05 g) (mother liquor crystals). The crystals contained 99.5% D(+)-CSA salts by weight.

(3) The third crystallization

The secondary crystals (80.0 g) prepared in the above (2) were dissolved in deionized water (28.8 ml). The resulting solution was seeded with crystals of D(+)-CARCN.D(+)-CSA and allowed to cool. The precipitated crystals were collected by filtration, washed with 90% aqueous ethanol (10 ml), and dried in vacuo to give crystals (62.6 g) (tertiary crystals). The crystals contained more than 99.9% D(+)-CSA salts by weight. The yield of D(+)-CSA salts was 49.4% on the basis of the starting DL-CARCN.D(+)-CSA. The physical properties of these crystals are shown in the following Table.

|  | Specific Rotation |
|---|---|
| Primary crystals | $[\alpha]_D^{20}$ + 23.3° (C = 4.4, H$_2$O) |
| Secondary crystals | $[\alpha]_D^{20}$ + 26.2° (C = 4.7, H$_2$O) m.p. 199–200° C. |
| Mother liquor crystals | $[\alpha]_D^{20}$ + 26.0° (C = 4.1, H$_2$O) m.p. 199–200° C. |
| Tertiary crystals | $[\alpha]_D^{20}$ + 26.6° (C = 4.5, H$_2$O) m.p. 199–201° C. |
| Mother liquor residue | $[\alpha]_D^{20}$ + 25.2° (C = 3.1, H$_2$O) |
| Tertiary crystals | |
| IR$\nu_{cm^{-1}}^{KBr}$: | 3270 (C—OH), 2330 (C≡N), 1740 (C=O), 1140–1200 (SO$_3^-$) |
| NMR$\delta_{90Mc}^{D_2O}$: | 4.76 (1H, m), 3.57 (1H, dd), 3.51 (1H, dd), 3.25 (9H, s), 3.08 (2H, q), 2.87 (1H, dd), 2.81 (1H, dd), 1.10–2.50 (7H, m), 1.05 (3H, s), 0.84 (3H, s) |

EXAMPLE 10

Fractional Crystallization Employing DL-CARCN.Cl at the Molar Ratio to DL-CARCN.D(+)-CSA of 1.25

(1) The first crystallization

A mixture of DL-CARCN.D(+)-CSA (200.0 g, 0.534 mole) and DL-CARCN.Cl (119.3 g, 0.668 mole) was dissolved in hot deionized water (90.4 ml). The resulting solution was seeded with crystals of D(+)-CARCN.D(+)-CSA at 80° C. and allowed to cool. The precipitated crystals were collected by filtration, washed with 90% aqueous ethanol (15 ml), and dried in vacuo to give crystals (172.9 g) (primary crystals). The crystals contained 95% D(+)-CSA salts by weight. The yield of D(+)-CSA salts was 82.2% on the basis of the starting DL-CARCN D(+)-CSA.

(2) The second crystallization

The crystals (160.0 g) prepared in the above (1) were dissolved in hot 80% aqueous ethanol (142 ml). The resulting solution was seeded with crystals of D(+)-CARCN.D(+)-CSA at 70° C. and allowed to cool. The precipitated crystals were collected by filtration, washed with 90% aqueous ethanol (15 ml), and dried in vacuo to give crystals (131.2 g) (secondary crystals). The crystals contained 99.7% D(+)-CSA salts by weight. The yield of D(+)-CSA salts was 70.7% on the basis of the starting DL-CARCN.D(+)-CSA. Subsequently the mother liquor was allowed to stand at 4° C. for 6 days to give crystals (3.41 g) (mother liquor crystals). The crystals contained 99.8% D(+)-CSA salts by weight.

(3) The third crystallization

The secondary crystals (90.0 g) prepared in the above (2) were dissolved in hot deionized water (37.8 ml). The resulting solution was seeded with crystals of D(+)-CARCN.D(+)-CSA and allowed to cool. The precipitated crystals were collected by filtration, washed with 90% aqueous ethanol (10 ml) and dried in vacuo to give crystals (65.2 g) (tertiary crystals). The crystals contained more than 99.9% D(+)-CSA salts by weight.

The yield of D(+)-CSA salts was 51.3% on the basis of the starting DL-CARCN.D(+)-CSA. The physical properties of these crystals are shown in the following Table.

|  | Specific Rotation |
| --- | --- |
| Primary crystals | $[\alpha]_D^{20}$ + 23.4° (C = 5.1, H$_2$O) |
| Secondary crystals | $[\alpha]_D^{20}$ + 25.6° (C = 4.7, H$_2$O) m.p. 198–199° C. |
| Mother liquor crystals | $[\alpha]_D^{20}$ + 25.8° (C = 4.3, H$_2$O) m.p. 198.5–199° C. |
| Tertiary crystals | $[\alpha]_D^{20}$ + 26.6° (C = 4.3, H$_2$O) m.p. 199–201° C. |
| Mother liquor residue | $[\alpha]_D^{20}$ + 24.9° (C = 4.1, H$_2$O) |

EXAMPLE 11

Fractional Crystallization Employing DL-CARCN.Cl at the Molar Ratio to DL-CARCN.D(+)-CSA of 1.2

A mixture of DL-CARCN.D(+)-CSA (6.00 g, 16.0 mmoles) and DL-CARCN.Cl (3.43 g, 19.2 mmoles) was dissolved in hot deionized water (2.8 ml). The resulting solution was seeded with crystals of D(+)-CARCN.-D(+)-CSA at 75° C. and allowed to cool. The precipitated crystals were collected by filtration, washed with methanol (1 ml), and dried in vacuo to give crystals (4.96 g, $[\alpha]_D^{20}$+22.7° (C=2.4, H$_2$O)). The crystals contained 90.6% D(+)-CSA salts by weight. The yield of D(+)-CSA salts was 74.8% on the basis of the starting DL-CARCN.D(+)-CSA.

EXAMPLE 12

Fractional Crystallization Employing DL-CARCN.Cl at the Molar Ratio to DL-CARCN.D(+)-CSA of 1.3

A mixture of DL-CARCN.D(+)-CSA (6.00 g, 16.0 mmoles) and DL-CARCN.Cl (3.72 g, 20.8 mmoles) was dissolved in hot deionized water (2.8 ml). The resulting solution was seeded with crystals of D(+)-CARCN.-D(+)-CSA at 78° C. and allowed to tool. The precipitated crystals were collected by filtration, washed with methanol (1 ml), and dried in vacuo to give crystals (5.43 g, $[\alpha]_D^{20}$+20.4° (C=2.7, H$_2$O)). The crystals contained 89.8% D(+)-CSA salts by weight. The yield of D(+)-CSA salts was 81.2% on the basis of the starting DL-CARCN.D(+)-CSA.

EXAMPLE 13

Fractional Crystallization Employing DL-CARCN.Cl at the Molar Ratio to DL-CARCN.D(+)-CSA of 1.4

A mixture of DL-CARCN.D(+)-CSA (6.00 g, 16.0 mmoles) and DL-CARCN.Cl (4.00 g, 22.4 mmoles) was dissolved in hot deionized water (2.8 ml). The resulting solution was seeded with crystals of D(+)-CARCN.-D(+)-CSA at 80° C. and allowed to cool. The precipitated crystals were collected by filtration, washed with methanol (1 ml), and dried in vacuo to give crystals (5.69 g, $[\alpha]_D^{20}$+19.5° (C=3.7, H$_2$O)). The crystals contained 87.7% D(+)-CSA salts by weight. The yield of D(+)-CSA salts was 83.2% on the basis of the starting DL-CARCN.D(+)-CSA.

EXAMPLE 14

Fractional Crystallization Employing D(DL-CARCN).L(+)-T and DL-CARCN.D(+)-CSA

DL-CARCN.Cl (69.0 g, 0.386 mole) dissolved in distilled water (100 ml) was passed through a column of a strong base anion exchange resin (1.16 mole equivalents; OH form). To the effluent solution, L(+)-T (29.0 g, 0.193 mole) was added and the pH of the resulting solution was adjusted to pH=9.0. The resulting solution was concentrated to dryness to give crude crystals (83.0 g, 98.8% yield) of D(DL-CARCN).L(+)-T($[\alpha]_D^{20}$+13.7°).

A mixture of D(DL-CARCN).L(+)-T (1.74 g, 4.00 mmoles) and DL-CARCN.D(+)-CSA (3.00 g, 8.00 mmoles) was dissolved in hot 50% aqueous methanol (1.8 ml). The resulting solution was seeded with crystals of D(+)-CARCN.D(+)-CSA and allowed to cool. The precipitated crystals were collected by filtration, washed with methanol (1 ml), and dried in vacuo to give crystals (3.11 g, $[\alpha]_D^{20}$+18.2° (C=1.8, H$_2$O)). The crystals contained 89.7% D(+)-CSA salts by weight. The yield of D(+)-CSA salts was 93.1% on the basis of the starting DL-CARCN.D(+)-CSA.

REFERENCE EXAMPLE 3

Preparation of D(+)-γ-trimethylamino-β-hydroxybutyrobetaine hydrochloride (D(+)-carnitine hydrochloride)

D(+)-CARCN.D(+)-CSA (80.0 g, 0.214 mole) was dissolved in 300 ml of deionized water, and the mixture was adjusted to pH=8.0 by addition of 1N-aqueous sodium hydroxide solution. To the resulting solution, 135 ml (1.17 moles) of 30% aqueous hydrogen perioxide solution was added, and the pH was adjusted to 8.0 in a similar manner under stirring at 10°–15° C. for over one hour. Then, the mixture was stirred at 25° C. for 3 hours. During the reaction, pH of the solution was maintained in a range of 8.0–9.0 by addition of 1N-aqueous hydrochloric acid solution or 1N-aqueous sodium hydroxide solution. The reaction mixture was cooled to 10°–15° C. and 2.0 g of manganese dioxide was added thereto. The solution was then stirred for one hour, neutralized by addition of 1N-aqueous hydrochloric acid solution and filtered. The filtrate was concentrated to dryness in vacuo to give an oil product (88.7 g). This oil product was dissolved in 250 ml of 3N-aqueous hydrochloric acid and reacted under continuous stirring at 80° C. for 3.6 hours. The resulting mixture was concentrated to dryness with a rotary evaporator to give 105 g of a residue.

The aqueous solution of this residue was passed through a column of 2600 ml (3.12 mole equivalents) of a weak basic anion exchange resin in OH form, and the effluent solution was adjusted to pH=1-2 by addition of 2N-aqueous hydrochloric acid solution. The resulting solution was concentrated to dryness with a rotary evaporator at 40°–45° C. to give 57.0 g of a residue. This residue was washed with acetone (500 ml) to give 48.5 g of residual solid. The washings were concentrated to give 7.80 g of an oil product. An aqueous solution of the oil product was passed through a column of 120 ml (0.12 mole equivalents) of a weak basic anion exchange resin in OH form, and the effluent solution was adjusted to pH=1-2 in a similar manner as above and concentrated to dryness to give 3.70 g of residual solid. These residual solids were combined and dissolved in methanol (50 ml), then insoluble salts were filtered off. The filtrate was concentrated and dried in vacuo to give crude crystals (41.6 g, 98.6% yield). These crude crystals were recrystallized from ethanol (54 ml) to give crystals (30.4 g, $[\alpha]_D^{20}+23.1°$ (C=3.5, H$_2$O)). The mother liquor was concentrated, and the residue was dissolved in 100 ml of 2N-aqueous hydrochloric acid solution, reacted at 65° C. for 1.5 hours, and concentrated to dryness. A residual oil product was washed with acetone to give 9.28 g of residual solid. The residual solid was recrystallized from 12 ml of ethanol to give 6.60 g of crystals ($[\alpha]_D^{20}+23.0°$ (C=3.1, H$_2$O)). The combined crystals (37.0 g) were recrystallized from 44.5 ml of ethanol to give crystals (31.8 g). A yield was 75.4% on the basis of the starting D(+)-CARCN.-D(+)-CSA. The physical properties of these crystals are shown in the following Table.

| m.p. 138–140° C. | |
| --- | --- |
| Specific rotation | $[\alpha]_D^{20}$ + 23.5 (C = 3.6, H$_2$O) |
| NMR$\delta_{90Mc}^{D_2O}$: | 4.68 (1H, m), 3.52 (1H, dd), 3.46 (1H dd), 3.24 (9H, s), 2.69 (1H, dd), 2.62 (1H, dd) |
| IR$\nu_{cm-1}^{KBr}$: | 3500, 3000, 1725 |

What is claimed is:

1. A method for resolving 2-(RS)-3-cyano-2-hydroxypropyltrimethyl-ammonium hydroxide, which comprises
    (1) mixing the racemic starting material with an optically active acid as a resolving agent in a solvent and concentrating the solution to dryness to form a mixture of two diastereomer salts;
    (2) mixing the racemic starting material with another acid which is different from the above resolving agent and concentrating the solution to dryness to form another mixture of two salts;
    (3) combining the four salts obtained from said two steps and dissolving the same in a hot resolving solvent;
    (4) seeding the resulting solution with crystals of the most crystallizable salt among the four salts;
    (5) cooling the above solution and crystallizing the crystals of the desired 2-(R) or 2-(S)-3-cyano-2-hydroxypropyltrimethylammonium salt through an exchange reaction between counter ions; and
    (6) collecting the crystals obtained from step 5 by filtration.

2. A method according to claim 1, wherein said optically active acid is 1-(S)-7,7-dimethyl-2-oxobicylo[2,2,1]heptane-1-methanesulfonic acid.

3. A method according to claim 1, wherein said optically active acid is 1-(R)-7,7-dimethyl-2-oxobicylo[2,2,1]heptane-1-methanesulfonic acid.

4. A method according to claim 1, wherein said optically active acid is (2R, 3R)-2,3-dihydroxybutanedioic acid.

5. A method according to claim 1, wherein said optically active acid is (2S,3S)-2,3-dihydroxybutanedioic acid.

6. A method according to claim 1, wherein said optically active acid is (2R,3R)-2,3-dibenzoylbutanedioic acid.

7. A method according to claim 1, wherein said optically active acid is (2S,3S)-2,3-dibenzoylbutanedioic acid.

8. A method according to claim 1, wherein said another acid different from the resolving agent is hydrogen chloride.

9. A method according to claim 2, wherein 2-(RS)-3-cyano-2-hydroxypropyltrimethylammonium chloride and 2-(RS)-3-cyano-2-hydroxypropyltrimethylammonium 1-(S)-7,7-dimethyl-2-oxobicyclo[2,2,1]heptane-1-methanesulfonate are dissolved in the resolving solvent and 2-(S)-3-cyano-2-hydroxypropyltrimethylammonium 1-(S)-7,7-dimethyl-2-oxo-bicyclo[2,2,1]heptane-1-methane-sulfonate is fractionally crystallized.

10. A method as claimed in claim 3, wherein 2-(RS)-3-cyano-2-hydroxypropyltrimethylammonium chloride and 2-(RS)-3-cyano-2-hydroxy-propyltrimethylammonium 1-(R)-7,7-dimethyl-2-oxobicyclo[2,2,1]heptane-1-methanesulfonate are dissolved in the resolving solvent and 2-(R)-3-cyano-2-hydroxypropyltrimethylammonium 1-(R)-7,7-dimethyl-2-oxobicyclo[2,2,1]heptane-1-methanesulfonate is fractionally crystallized.

* * * * *